US006679103B1

United States Patent
Sadler

(10) Patent No.: US 6,679,103 B1
(45) Date of Patent: Jan. 20, 2004

(54) CONTINUOUS FLOW MOISTURE ANALYZER FOR DETERMINING MOISTURE CONTENT IN LIQUID SAMPLE MATERIAL

(75) Inventor: William G. Sadler, Scottsdale, AZ (US)

(73) Assignee: Arizona Instrument LLC, Tempe, AZ (US)

( * ) Notice: Subject to any disclaimer, the term of this patent is extended or adjusted under 35 U.S.C. 154(b) by 203 days.

(21) Appl. No.: 09/708,108

(22) Filed: Oct. 31, 2000

(51) Int. Cl.[7] .............................................. G01N 25/56
(52) U.S. Cl. ........................... 73/73; 73/29; 250/339.1; 324/643
(58) Field of Search .................... 73/29, 73; 250/339.1; 324/643

(56) References Cited

U.S. PATENT DOCUMENTS 4,838,705 A  6/1989  Byers, Jr. et al. ............. 374/14
5,712,421 A  * 1/1998 Raisanen .................. 73/19.01

* cited by examiner

Primary Examiner—Hezron Williams
Assistant Examiner—André K. Jackson
(74) Attorney, Agent, or Firm—Richard E. Oney; Fennemore Craig, PC; Jordan M. Meschkow

(57) ABSTRACT

A continuous flow moisture analyzer (20) determines moisture content in a liquid sample material (46). The moisture analyzer (20) includes an injection system (44) for delivering the liquid sample material (46) at a controlled rate. The injection system includes an injector tube (48). An evaporator (52) has a first end (50) for receiving the injector tube (48) and a second end (56). The injector tube (148) provides the liquid sample material (46) to the evaporator (52) at the first end (50). A carrier gas inlet (54) is in fluid communication with the second end (56) of the evaporator (52) for providing a carrier gas (58) to the evaporator (52) at the second end (56). The carrier gas (58) absorbs moisture from the liquid sample material (46) in the evaporator (52). A relative humidity sensor (78) in fluid communication with the evaporator (52) detects the moisture in the carrier gas (58).

19 Claims, 4 Drawing Sheets

CONTINUOUS FLOW MOISTURE ANALYZER FOR DETERMINING MOISTURE CONTENT IN LIQUID SAMPLE MATERIAL

TECHNICAL FIELD OF THE INVENTION

The present invention relates generally to moisture analyzers. More specifically, the present invention relates to a continuous flow moisture analyzer for determining the moisture content in a liquid sample material under test.

BACKGROUND OF THE INVENTION

Various manufacturing processes, chemical reactions, and laws attendant certain industries require that the percentage of certain volatile fluids of interest present within a product be known. Indeed, the determination of moisture (or volatile) content in materials is of such importance in so many fields that a variety of devices and analytical methods have been developed to provide such information.

Moisture analysis devices include, for example, vacuum ovens and convection ovens which heat a test sample of the product to a temperature commensurate with the volatile fluid of interest to cause evaporation of such fluid. Devices of this type are often referred to as loss on drying analyzers. Using a loss on drying moisture analyzer, the resulting reduction in weight of the test sample provides data for computing the percent by weight of the volatile fluid of interest in the test sample. Various computational techniques may be employed to forecast the percentage determination based upon the initial weight loss rate. Such computational approximations reduce the time required to complete a test without serious derogation of the accuracy of the determination. Loss on drying techniques are limited to approximately 0.1% minimum moisture loss due to secondary effects such as convective air currents, buoyancy effects, and temperature gradients. In addition, loss on drying techniques can incur some degree of measurement error relative to the accuracy of the scale used for weighing the test sample.

Other moisture analysis devices employ sensors that measure the quantity of volatile fluid in a gas stream to determine the amount of volatile fluid in a test sample. For example, one such moisture analyzer includes a test sample heater, a dry carrier gas flow system, and a moisture transducer. The moisture analyzer heats a sample of test material contained in a septum bottle. The dry gas is injected into the septum bottle and absorbs the moisture out of the sample material. The dry gas, carrying the moisture from the sample, is ejected from the septum bottle and transported to the moisture transducer where the moisture content of the flowing gas is measured. A processor then integrates the varying moisture signal and converts the integrated signal to total moisture content. Using the sample weight and the total moisture content value, the moisture concentration in the test sample is subsequently calculated.

Unfortunately, problems with moisture analysis devices such as pre-existing moisture levels, transient response times, and contamination can render the measurement of moisture content inaccurate. In one moisture analyzer, uncontrolled moisture can be introduced into the dry carrier gas flow system. This uncontrolled moisture results in a non-consistent baseline, which consequently leads to inaccuracy in the measurement of the moisture content in the sample material.

In some manufacturing environments, the test sample under consideration is a liquid sample material such as petroleum products, oils, liquid silicon, liquid chemicals, liquid food products, and so forth. Additional problems exist with the use of moisture analysis devices to determine the moisture content in these liquid sample materials. The moisture may be water contamination or another liquid contaminant in the liquid sample material. For example, in test situations in which water is the volatile fluid of interest present within the liquid sample material, loss on drying techniques may be rendered inaccurate because such techniques eliminate all volatile liquids rather than just the water. In addition, when a liquid sample material is placed in the septum bottle discussed above, the ratio of the surface area to volume of the liquid sample material may be insufficient for enabling the dry gas to efficiently absorb the water from the liquid sample material.

An analytical moisture analysis method known as the Karl Fischer moisture analysis technique is a method of titrating a test sample with a reagent to determine trace amounts of water in the test sample. Karl Fischer titration employs a specific reaction to consume water, independent of the presence of other volatile substances, and can be used to determine the moisture content in liquid sample materials. Unfortunately, chemical analysis methods, such as Karl Fischer titration, rely on the use of various reagents which may be toxic. Moreover, such chemical analysis methods usually require very skilled operators and are often quite time consuming.

SUMMARY OF THE INVENTION

Accordingly, it is an advantage of the present invention that a continuous flow moisture analyzer is provided.

It is another advantage of the present invention the continuous flow moisture analyzer efficiently and accurately determines the moisture content in a liquid sample material.

It is another advantage of the present invention that the continuous flow moisture analyzer enables moisture to be effectively evolved from a liquid sample material.

It is yet another advantage of the present invention that the continuous flow moisture analyzer accurately determines the moisture content in a liquid sample material by substantially preventing the introduction of uncontrolled moisture in a gas flow system of the moisture analyzer.

The above and other advantages of the present invention are carried out in one form by a continuous flow moisture analyzer for determining moisture content in a liquid sample material. The moisture analyzer includes an injection system for delivering the liquid sample material, the injection system including an injector tube. An evaporator has a first end for receiving the injector tube and a second end. The injector tube provides the liquid sample material to the evaporator at the first end. A carrier gas inlet in fluid communication with the second end of the evaporator provides a carrier gas to the evaporator at the second end. The carrier gas absorbs moisture from the liquid sample material in the evaporator. A moisture sensor in fluid communication with the evaporator detects the moisture in the carrier gas.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
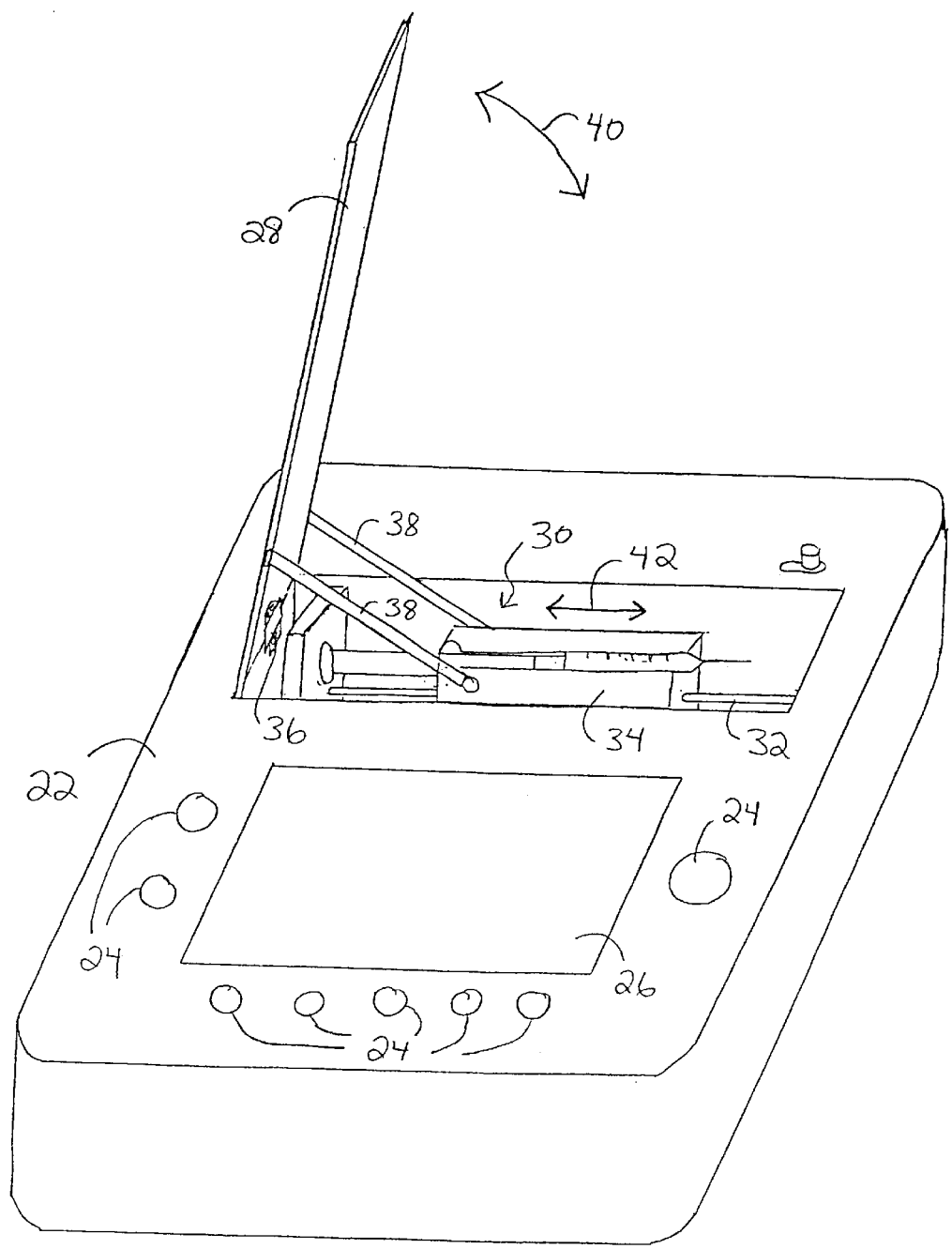
FIG. 1 shows a perspective view of a continuous flow moisture analyzer in accordance with a preferred embodiment of the present invention.

FIG. 1 shows a perspective view of a continuous flow moisture analyzer 20 in accordance with a preferred embodiment of the present invention. Moisture analyzer 20 is used primarily for determining the moisture content, i.e., the volatile liquid such as water, in a liquid sample material under test. Exemplary liquid sample materials include petroleum products, oils, liquid silicon, liquid chemicals, liquid food products, and so forth. Moisture analyzer 20 is configured to evaporate the moisture, such as water, present within a liquid sample material. This moisture is absorbed by a carrier gas passing by the liquid sample material. The carrier gas is transported to a moisture sensor, which subsequently detects the moisture in the carrier gas.

Moisture analyzer 20 includes a chassis 22 having an input element 24 and an output element 26. Input element 24 can encompass pushbuttons (as shown), a keypad, keyboard, mouse, pointing device, or other devices providing input to moisture analyzer 20. Such input may include, for example, liquid material sample identification, lot or product ID number, test parameters, test duration, and so forth. Output element 26 can encompass a display (as shown), a printer, a printer port, or other devices providing output from moisture analyzer 20. Such output may include, material sample identification, test results in parts-per-million, test results in percent moisture, test results in total micrograms of water, and so forth.

Chassis 22 further includes a cover 28 enclosing a chamber 30 within moisture analyzer 20. A track 32, in fixed relation to moisture analyzer 20, and a tray 34, slidably coupled to track 32, are positioned in chamber 30. Cover 28 includes a hinge element 36 coupled to moisture analyzer 20 and links 38 coupled to tray 34. Cover 28 may optionally include a viewing window (not shown) to allow visual observation inside of chamber 30 when cover 28 is closed. When cover 28 is pivoted about hinge element 36, as indicated by an arrow 40, links 38 cause tray 34 to slide along track 32, as indicated by an arrow 42. This sliding action will be discussed in greater detail below.

Figure 2:
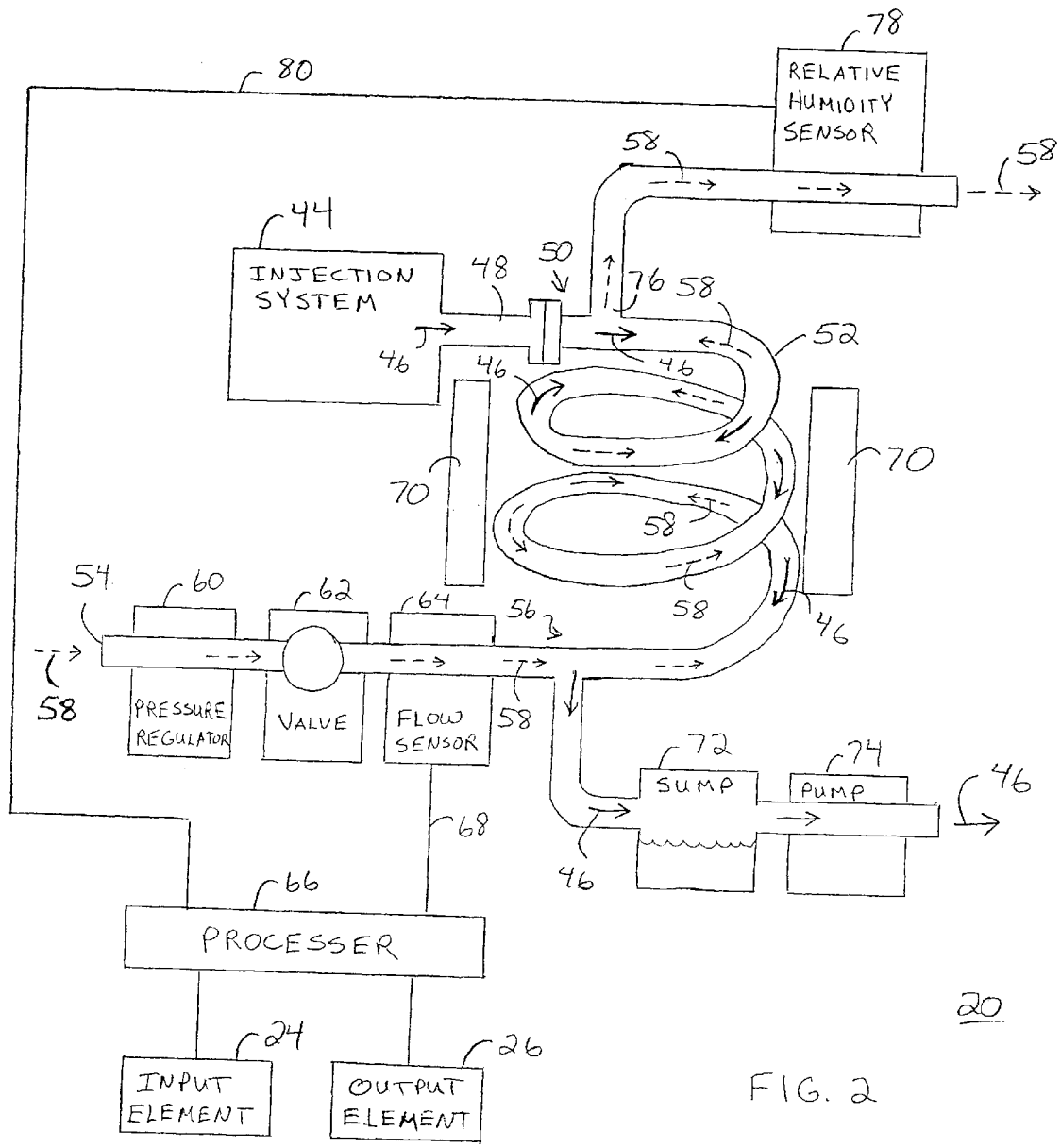
FIG. 2 shows a block diagram of the continuous flow moisture analyzer.

FIG. 2 shows a block diagram of continuous flow moisture analyzer 20. Moisture analyzer 20 includes an injection system 44 configured to deliver a liquid sample material, represented by solid arrows 46, via an injector tube 48 of injection system 44 to a first end 50 of an evaporator 52. A carrier gas inlet 54 is in fluid communication with a second end 56 of evaporator 52 for providing a carrier gas, represented by dashed arrows 58 to evaporator 52.

In particular, carrier gas inlet 54 provides carrier gas 58 to a pressure regulator 60 configured to receive a flow of carrier gas 58. Carrier gas 58 may be dry nitrogen, dry air, or any other gas that can effectively absorb and carry moisture. Pressure regulator 60 provides carrier gas 58 to a valve 62 at a predetermined pressure. In a preferred embodiment, the predetermined pressure is approximately one and a half pounds per square inch.

Valve 62 is a restrictor valve that receives carrier gas 58 output by pressure regulator 60 and provides carrier gas 58 at a controlled flow rate. In particular, valve 62 has an orifice of approximately 0.15 mm (0.006 inches) for controlling the flow rate of carrier gas 58 to approximately one hundred milliliters per minute.

An output of valve 62 is in communication with a flow sensor 64. Flow sensor 64 measures a mass flow of carrier gas 58 as carrier gas 58 passes flow sensor 64. The mass flow is the mass of a fluid substance (e.g., carrier gas 58) that passes a specified unit area in a unit amount of time. Flow sensor 64 has an output in communication with a processor 66 for providing a mass flow signal 68, responsive to the flow rate of carrier gas 58, through an analog-to-digital converter (not shown) to processor 66. Flow sensor 64 is in communication with second end 56 of evaporator 52 for, providing carrier gas 58 to evaporator 52 at a predetermined pressure and flow rate.

A heater 70 surrounds evaporator 52 and is configured to heat liquid sample material 46 to a predetermined temperature at a predetermined rate to evaporate the volatile liquid from liquid sample material 46. The predetermined temperature and rate, controlled by processor 66, depend upon the characteristics of both liquid sample material 46 and the volatile liquid of interest. A resistive temperature device (not shown) may be used to read the temperature of heater 70. Controls for the various sequential steps, pressure, flow rates, predetermined temperature and rate, and so forth are performed by processor 66.

Liquid sample material 46, delivered by injection system 44, flows from first end 50 of evaporator 52 to second end 56 of evaporator 52. A sump 72 is coupled to second end 56 for collecting liquid sample material 46. A pump 74, coupled to sump 72, may be used to evacuate liquid sample material 46 from moisture analyzer 20.

Carrier gas 58, provided by carrier gas inlet 54, flows from second end 56 of evaporator 52 to first end 50 of evaporator 52. As liquid sample material 46 flows from first end 50 to second end 56, and carrier gas 58 flows from second end 56 to first end 50, carrier gas 58 absorbs evolved moisture from liquid sample material 46 as liquid sample material 46 is heated.

Evaporator 52 is a coil evaporator. The coil configuration of evaporator 52 advantageously maximizes the surface area of material 46 to the volume of liquid sample material 46 to efficiently facilitate the evolution of the moisture from liquid sample material 46. In addition, the coil configuration results in a compact size of evaporator 52 so that the overall dimensions of moisture analyzer 20 can be kept as small as possible. Furthermore, the coil configuration of evaporator 52 causes liquid sample material 46 to flow from first end 50 to second end 56 due to the effect of gravity. However, carrier gas 58 flows from second end 56 to first end 50 in response to a pressure difference between second end 56 and first end 50. Thus, carrier gas 58 has an optimal opportunity to absorb moisture evolved from liquid sample material 46.

Although evaporator 52 is described in terms of a coil evaporator, it should be understood that other evaporator configurations may be employed. For example, an evaporator having a screen configuration may be used to provide a high surface area to volume ratio of liquid sample material 46.

Carrier gas 58 is expelled from an outlet 76 at first end 50 of evaporator 52. Carrier gas 58 flows from outlet 76 to a relative humidity sensor 78. Relative humidity sensor 78 is a moisture sensor for detecting moisture in carrier gas 58.

Relative humidity sensor 78 has an output in communication with processor 66 for providing a percent relative humidity signal 80, responsive to the relative humidity of carrier gas 58, through an analog-to-digital converter (not shown) to processor 66.

In a preferred embodiment, moisture analyzer 20 employs a relative humidity sensor. However, is should be apparent that other moisture sensors may be used. In addition, a moisture detecting reagent maybe used as a moisture sensor in an alternative embodiment of the present invention.

During the heating of liquid sample material 46 within evaporator 52, particulate matter of liquid sample material 46 may be inadvertently conveyed by carrier gas 58. Such particulate matter may jeopardize the integrity and accuracy of analysis of the moisture in carrier gas 58 and/or undesirably cause particulate matter to be exhausted from moisture analyzer 20 with carrier gas 58. To eliminate such particulate matter, a filter (not shown)may be interposed between outlet 76 and relative humidity sensor 78 to filter carrier gas 58 flowing from outlet 76.

Processor 66 subsequently computes a moisture content of carrier gas 58 as a volume per unit of time in response to mass flow signal 68 received from flow sensor 64 and percent relative humidity signal 80 received from relative humidity sensor 78 Following detection of the moisture content in carrier gas 58, carrier gas 58 is exhausted from continuous flow moisture analyzer 20.

Figure 3:
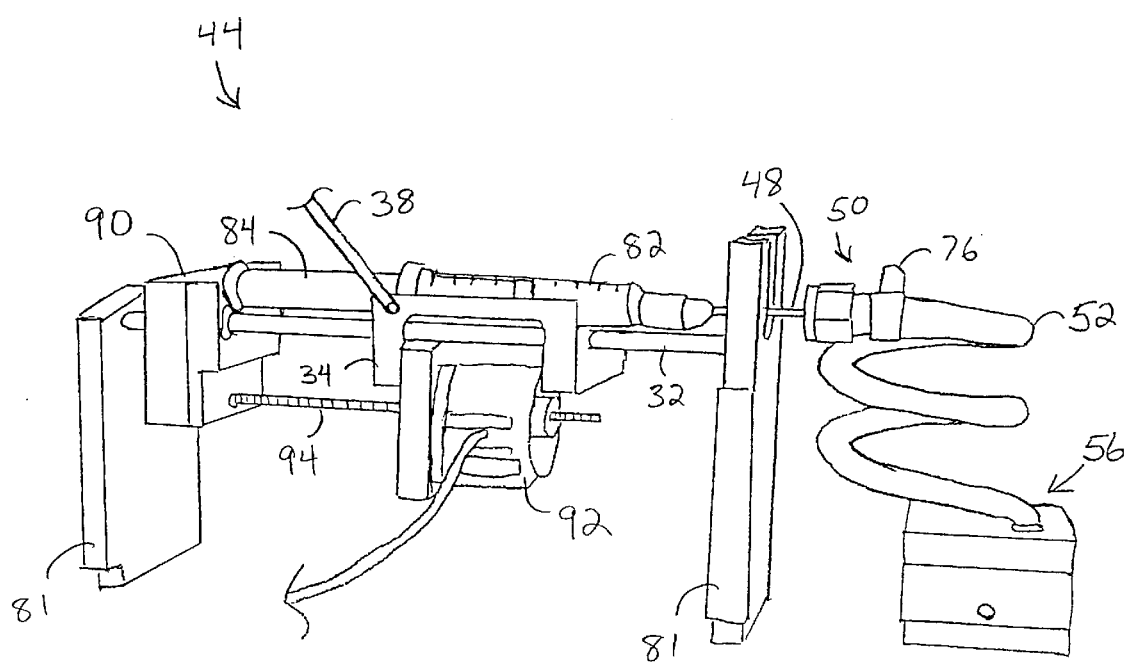
FIG. 3 shows a perspective view of an injection system of the continuous flow moisture analyzer engaged with an evaporator of the continuous flow moisture analyzer.

FIG. 3 shows a perspective view of injection system 44 engaged with evaporator 52 of continuous flow moisture analyzer 20. As discussed previously, injection system 44 includes tray 34 slidably coupled to track 32. Track 32 is coupled to braces 81 which are attached to an interior surface of moisture analyzer 20 so that track 32 cannot move relative to moisture analyzer 20. Links 38 of cover 28 (FIG. 1) are coupled to tray 34.

Injection system 44 further includes a hollow cylinder 82 for retaining liquid sample material 46 (FIG. 2). Injector tube 48, in the form of a needle, is coupled to hollow, cylinder 82. A plunger 84 is inserted into hollow cylinder 821 for pushing against liquid sample material 46 to eject liquid sample material 46 from injection system 44. Thus, hollow cylinder 82, plunger 84, and injector tube 48 combine to form a needle and syringe. For clarity of illustration injector tube 48 will be referred to hereinafter as needle 48.

Figure 4:
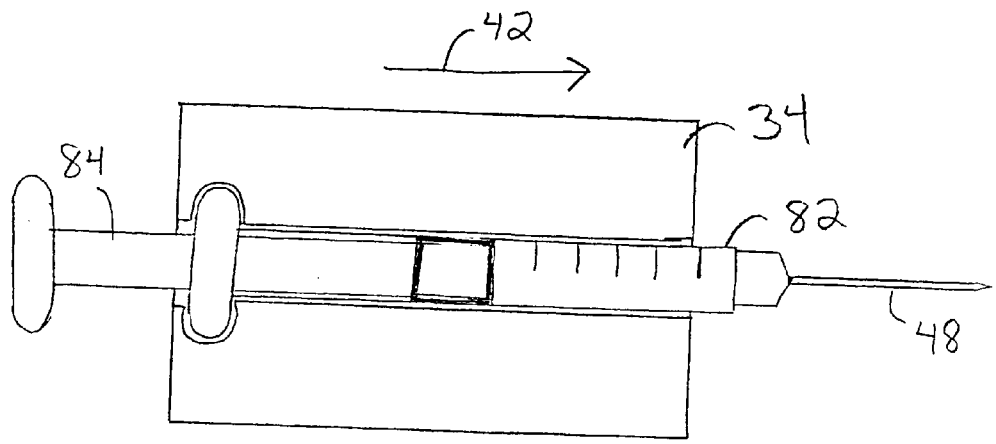
FIG. 4 shows a top view of a tray of the injection system of FIG. 3.

FIG. 4 shows a top view of tray 34 of injection system 44. Tray 34 is accessible by opening cover 28 (FIG. 1) to expose chamber 30 (FIG. 1) in which tray 34 is positioned. Tray 34 includes a groove optimally shaped to hold hollow cylinder 82 substantially motionless relative to tray 34. The groove in tray 34 is further shaped to allow movement of plunger 84 so that plunger 84 is free to push against liquid sample material 46.

In operation, a technician draws liquid sample material 46 (FIG. 1) into hollow cylinder 82 through a channel 86 (see FIG. 5) in needle 48 by drawing back on plunger 82. Once a predetermined volume of liquid sample material 46 is held in hollow cylinder 82, hollow cylinder 82, in combination with plunger 82 and needle 48, is seated in the groove in tray 34. In a preferred embodiment, the technician may draw approximately five cubic centimeters of liquid sample material 46 into hollow cylinder 82.

Figure 5:
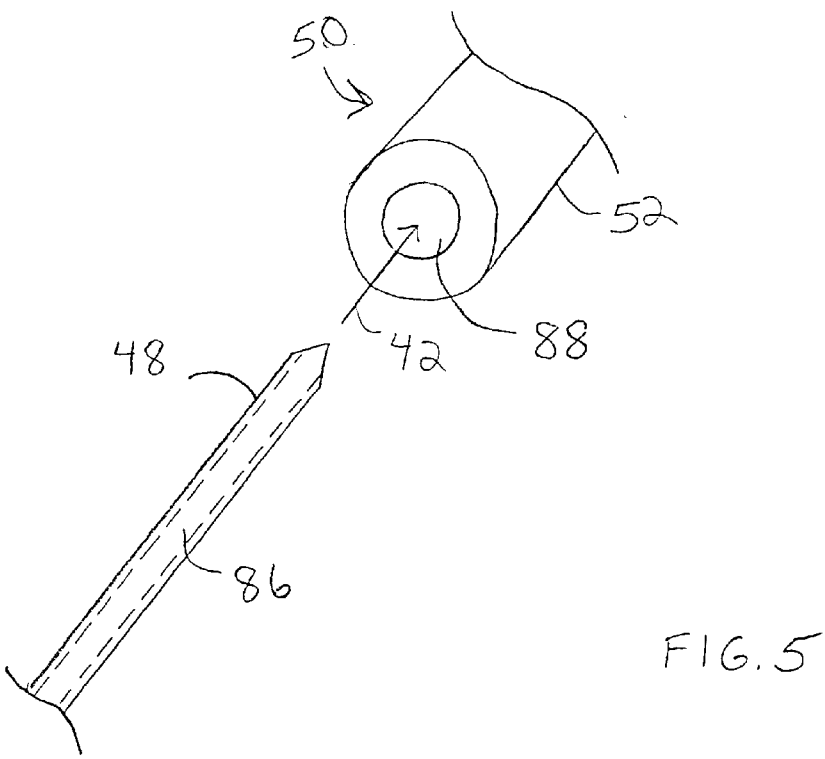
FIG. 5 shows a perspective view of a needle of the injection system for penetrating a septum of an evaporator of the continuous flow moisture analyzer.

FIG. 5 shows a perspective view of needle 48 of injection system 44 for penetrating a septum 88 of evaporator 52. Septum 88 is a thin wall of material, such as rubber or silicon, located at first end 50 of evaporator 52. Septum 88 functions to seal evaporator 52 at first end 50 from the introduction of uncontrolled moisture in the environment outside of analyzer 20 (FIG. 1).

When cover 28 (FIG. 1) is rotated about hinge element 36 (FIG. 1) to close cover 28, links 38 (FIG. 1) push against tray 34 causing tray 34 to slide along track 32 (FIG. 1). Needle 48, coupled to hollow chamber 82 seated in the groove in tray 34, slides toward first end 50 of evaporator 52 and penetrates septum 88 to engage needle 48 with evaporator 52.

Referring back to FIG. 3, injection system 44 further includes an actuator mechanism 90 in contact with plunger 84. A motor 92 is coupled to actuator mechanism 90 via a shaft 94. In a preferred embodiment, motor 92 is a stepper motor that rotates shaft 94 in fixed angular steps. The rotation of shaft 94 drives actuator mechanism 90 against plunger 84. Consequently, when motor 92 is activated, plunger 84 pushes against liquid sample material 46 (FIG. 2) in hollow cylinder 82 to eject liquid sample material 46 from hollow cylinder 82 via channel 86 (FIG. 5) in needle 48 at a controlled rate. In an exemplary embodiment, motor 92 moves actuator mechanism slowly so that a volume of liquid sample material 46 of approximately five cubic centimeters is ejected from hollow cylinder 82 and introduced into evaporator 52 over a duration of approximately five to ten minutes.

In a standby mode operation, moisture analyzer 20 (FIG. 1) is activated in one of two configurations. A first configuration is with cover 28 (FIG. 1) open so that needle 48 cannot penetrate septum 88 (FIG. 5). A second configuration is with cover 28 closed so that needle 48 penetrates septum 88 but stepper motor 92 is inactivated so that actuator mechanism 90 does not drive plunger 84. When moisture analyzer 20 is activated in the standby mode, carrier gas 58 (FIG. 2) flows into evaporator 52 at second end 56. Carrier gas 58 is expelled from outlet 76 at first end 50 of evaporator 52 and is subsequently transported to relative humidity sensor 78 (FIG. 2) to determine a baseline moisture content of continuous flow moisture analyzer 20. Moisture analyzer 20 may remain activated continuously in which case carrier gas 58 will flow through the system continuously. Alternatively, moisture analyzer 20 may be activated some predetermined period of time prior to performing moisture analysis of sample material 46 (FIG. 1).

Active mode operation is initiated following standby mode operation so that carrier gas 58 (FIG. 2) continuously flows during the entirety of both standby mode and active mode operations. In active mode, motor 92 is activated to drive actuator mechanism 90 against plunger 84 to eject liquid sample material 46 from hollow cylinder 82. Once actuator mechanism 90 is actuated, liquid sample material 46 (FIG. 2) is provided to evaporator 52. In addition, heater 70 is activated so that moisture begins evolving from liquid sample material 46. Carrier gas 58 continuously flowing from second end 56 to first end 50 begins absorbing moisture evolving from liquid sample material 46 in evaporator 52.

Carrier gas 58 carrying moisture from liquid sample material 46 is expelled from outlet 76 and transported to relative humidity sensor 78 (FIG. 2) where the moisture in carrier gas 58 is detected. Mass flow signal 68 (FIG. 2) and percent relative humidity signal 80. (FIG. 2) are used by processor 66 (FIG. 1) to obtain a moisture figure related to the amount of volatile liquid, or moisture, in sample material 50. Carrier gas 58 carrying moisture from liquid sample material 46 is subsequently exhausted from analyzer 20. Likewise, liquid sample material 46 is subsequently evacuated from analyzer 20 via sump 72 (FIG. 2) and pump 74 (FIG. 2) with its moisture given up.

The moisture content of carrier gas 58 is computed relative to a baseline moisture content of carrier gas 58. In other words, processor 66 initially computes a moisture content of carrier gas 58 in the standby mode, i.e., prior to liquid sample material 46 (FIG. 2) being introduced into evaporator 52. The moisture content of carrier gas 58 is then computed in an active mode, i.e., after needle 48 has penetrated septum 88 and liquid sample material 46 is introduced into evaporator 52. Processor 66 subsequently computes a difference from the baseline moisture content responsive to the moisture detected during the active mode to obtain a moisture content of liquid sample material 46.

In an alternative embodiment of the present invention, continuous flow moisture analyzer may be adapted for use in high volume liquid transfer situations to monitor for moisture contamination in a large portion of or the entire volume of the liquid to be transferred. Such monitoring may be highly desirable to ascertain the quality of the liquid being transferred and to ensure that the liquid being transferred does not contain excess moisture. Exemplary high volume liquid transfer situations may include, for example, the transfer of oil in an oil pipeline, transfer of a liquid chemical into or out of a tanker truck, transfer of milk or other liquid food product into or out of a holding tank, and so forth. In this alternative embodiment, the injection system of the present moisture analyzer would be adapted to accommodate the controlled flow of a large volume of liquid into an evaporator system. Likewise, the evaporator system and flow characteristics (i.e., pressure and flow rate) of the carrier gas would be adapted to facilitate evolution of moisture from this larger volume of liquid. An output of such a moisture analyzer may be a chart that reveals the percent moisture of the liquid for an entire fluid transfer.

In summary, the present invention teaches of a continuous flow moisture analyzer for determining moisture content in a liquid sample material. The sealed evaporator and the controlled flow of the liquid sample material into the evaporator results in an analyzer that efficiently and accurately determines the moisture content in a sample of liquid test material. Furthermore, the coil configuration of the evaporator and the controlled flow of the liquid sample material through the evaporator enables the moisture to be effectively evolved from the liquid sample material. In addition, the moisture analyzer accurately determines the moisture content in the sample material by substantially preventing the introduction of uncontrolled moisture in the gas flow system of the moisture analyzer.

Although the preferred embodiments of the invention have been illustrated and described in detail, it will be readily apparent to those skilled in the art that various modifications may be made therein without departing from the spirit of the invention or from the scope of the appended claims.

What is claimed is:

1. A continuous flow moisture analyzer for determining moisture content in a liquid sample material, the moisture analyzer comprising:
    an injection system for delivering the liquid sample material to an evaporator, the injection system including:
        a hollow cylinder for retaining the liquid sample material;
        an injector tube coupled to an end of the hollow cylinder; and
        a plunger inserted into the hollow cylinder for pushing against the liquid sample material to eject the liquid sample material through a channel in the injector tube into the evaporator;
    the evaporator having a first end for receiving the injector tube and having a second end, the injector tube providing the liquid sample material to the evaporator at the first end;
    a carrier gas inlet in fluid communication with the second end of the evaporator for providing a carrier gas to the evaporator at the second end, the carrier gas absorbing moisture from the liquid sample material in the evaporator; and
    a moisture sensor in fluid communication with the evaporator for detecting the moisture in the carrier gas.

2. A continuous flow moisture analyzer as claimed in claim 1 wherein the injection system further includes:
    an actuator mechanism in contact with the plunger; and
    a motor coupled to the actuator mechanism for driving the actuator mechanism against the plunger to eject the liquid sample material from the hollow cylinder.

3. A continuous flow moisture analyzer as claimed in claim 1 wherein the injection system further includes:
    a track in fixed relation with the evaporator; and
    a tray for holding the hollow cylinder, the tray being slidably coupled to the track, and the tray being configured to slide along the track to engage the injector tube with the evaporator at the first end.

4. A continuous flow moisture analyzer as claimed in claim 3 further comprising a cover enclosing a chamber in the moisture analyzer, the track and the tray being positioned in the chamber, the cover including a hinge element coupled to the moisture analyzer and a link coupled to the tray, wherein when the cover is pivoted about the hinge element the link causes the tray to slide along the track.

5. A continuous flow moisture analyzer for determining moisture content in a liquid sample material, the moisture analyzer comprising:
    an injection system for delivering the liquid sample material, the injection system including an injector tube;
    an evaporator having a first end for receiving the injector tube and having a second end, the injector tube providing the liquid sample material to the evaporator at the first end;
    a carrier gas inlet in fluid communication with the second end of the evaporator for providing a carrier gas to the evaporator at the second end, the carrier gas, absorbing moisture from the liquid sample material in the evaporator; and
    a moisture sensor in fluid communication with the evaporator for detecting the moisture in the carrier gas;
    wherein the first end includes a septum and the injector tube is a needle, the needle penetrating the septum to provide the liquid sample material to the evaporator.

6. A continuous flow moisture analyzer for determining moisture content in a liquid sample material, the moisture analyzer comprising:
    an injection system for delivering the liquid sample material, the injection system including an injector tube;
    an evaporator comprising a continuous coil having a first end for receiving the injector tube and having a second end, the injector tube providing the liquid sample material to the evaporator at the first end;
    a carrier gas inlet in fluid communication with the second end of the evaporator for providing a carrier gas to the evaporator at the second end, the carrier gas absorbing moisture from the liquid sample material in the evaporator; and a moisture sensor in fluid communication with the evaporator for detecting the moisture in the carrier gas.

7. A continuous flow moisture analyzer as claimed in claim 1 further comprising a pressure regulator interposed between the carrier gas inlet and the second end of the evaporator for providing the carrier gas to the evaporator at a predetermined pressure.

8. A continuous flow moisture analyzer as claimed in claim 1 further comprising a valve interposed between the carrier gas inlet and the second end of the evaporator for providing the carrier gas to the evaporator at a predetermined flow rate.

9. A continuous flow moisture analyzer as claimed in claim 1 further comprising a mass flow sensor in fluid communication with the carrier gas inlet for measuring a flow rate of the carrier gas entering the evaporator.

10. A continuous flow moisture analyzer as claimed in claim 1 further comprising a heater surrounding the evaporator for heating the liquid sample material to evolve the moisture from the liquid sample material.

11. A continuous flow moisture analyzer for determining moisture content in a liquid sample material, the moisture analyzer comprising:
   an injection system for delivering the liquid sample material, the injection system including an injector tube providing the liquid sample material to the evaporator at the first end;
   an evaporator having a first end for receiving the injector tube and having a second end in fluid communication with a carrier gas inlet for providing a carrier gas to the evaporator at the second end;
   a moisture sensor in fluid communication with the evaporator for detecting the moisture in the carrier gas;
   wherein the carrier gas flows from the second end to the first end of the evaporator and absorbs moisture from the liquid sample material in the evaporator and the moisture sensor is in fluid communication with the evaporator proximate the first end.

12. A continuous flow moisture analyzer as claimed in claim 11 wherein the liquid sample material flows from the first end to the second end of the evaporator, and the moisture analyzer further comprises a sump coupled to the second end of the evaporator for collecting the liquid sample material.

13. A continuous flow moisture analyzer for determining moisture content in a liquid sample material, the moisture analyzer comprising:
   an injection system for delivering the liquid sample material, the injection system including:
      a hollow cylinder for retaining the liquid sample material;
      a needle coupled to an end of the hollow cylinder; and
      a plunger inserted into the hollow cylinder for pushing against the liquid sample material to eject the liquid sample material through a channel in needle;
   an evaporator having a first end and a second end, the first end including a septum, the needle penetrating the septum to provide the liquid sample material to the evaporator;
   a carrier gas inlet in fluid communication with the second end of the evaporator for providing a carrier gas to the evaporator at the second end, the carrier gas absorbing moisture from the liquid sample material in the evaporator; and
   a moisture sensor in fluid communication with the evaporator for detecting the moisture in the carrier gas.

14. A continuous flow moisture analyzer as claimed in claim 13 wherein the injection system further includes:
   an actuator mechanism in contact with the plunger; and
   a motor coupled to the actuator mechanism for driving the actuator mechanism against the plunger to eject the liquid sample material from the hollow cylinder.

15. A continuous flow moisture analyzer as claimed in claim 13 wherein the injection system further includes:
   a track in fixed relation with the evaporator; and
   a tray for holding the hollow cylinder, the tray being slidably coupled to the track, and the tray being configured to slide along the track to cause the needle to penetrate the septum.

16. A continuous flow moisture analyzer as claimed in claim 15 further comprising a cover enclosing a chamber in the moisture analyzer, the track and the tray being positioned in the chamber, the cover including a hinge element coupled to the moisture analyzer and a link coupled to the tray, wherein when the cover is pivoted about the hinge element the link causes the tray to slide along the track.

17. A continuous flow moisture analyzer for determining moisture content in a liquid sample material, the moisture analyzer comprising:
   an injection system for delivering the liquid sample material, the injection system including an injector tube;
   a continuous coil evaporator having a first end for receiving the injector tube and having a second end, the injector tube providing the liquid sample material to the evaporator at the first end;
   a heater surrounding the continuous coil evaporator for heating the liquid sample material to evolve moisture from the liquid sample material;
   a carrier gas inlet in fluid communication with the second end of the evaporator for providing a carrier gas to the evaporator at the second end, the carrier gas absorbing the evolved moisture; and
   a moisture sensor in fluid communication with the evaporator for detecting the evolved moisture in the carrier gas.

18. A continuous flow moisture analyzer as claimed in claim 17 wherein the carrier gas flows from the second end to the first end of the evaporator, and the moisture sensor is in fluid communication with the evaporator proximate the first end.

19. A continuous flow moisture analyzer as claimed in claim 17 wherein the liquid sample material flows from the first end to the second end of the evaporator, and the moisture analyzer further comprises a sump coupled to the second end of the evaporator for collecting the liquid sample material.

* * * * *